(12) United States Patent
Crites-Bachert (10) Patent No.: US 11,975,205 B2
(45) Date of Patent: *May 7, 2024

(54) PERCUTANEOUS NERVE EVALUATION FOR SACRAL NEUROMODULATION

(71) Applicant: Resolute 360 LLC, Happy Valley, OR (US)

(72) Inventor: Melanie Crites-Bachert, Gresham, OR (US)

(*) Notice: Subject to any disclaimer, the term of this patent is extended or adjusted under 35 U.S.C. 154(b) by 0 days.

This patent is subject to a terminal disclaimer.

(21) Appl. No.: 18/149,763

(22) Filed: Jan. 4, 2023

(65) Prior Publication Data

US 2023/0166116 A1 Jun. 1, 2023

Related U.S. Application Data

(63) Continuation of application No. 17/083,774, filed on Oct. 29, 2020, now Pat. No. 11,648,405.

(51) Int. Cl.
| | |
|---|---|
| *A61N 1/37* | (2006.01) |
| *A61B 17/34* | (2006.01) |
| *A61N 1/05* | (2006.01) |
| *A61N 1/36* | (2006.01) |
| *A61N 1/372* | (2006.01) |
| *A61B 90/00* | (2016.01) |

(52) U.S. Cl.
CPC .......... *A61N 1/372* (2013.01); *A61B 17/3403* (2013.01); *A61B 17/3468* (2013.01); *A61N 1/0551* (2013.01); *A61N 1/36062* (2017.08); *A61B 2090/395* (2016.02); *A61B 2090/3966* (2016.02); *A61B 2090/3983* (2016.02)

(58) Field of Classification Search
CPC .. A61N 1/372; A61N 1/36062; A61N 1/0551; A61B 17/3403; A61B 17/3468; A61B 2090/385; A61B 2090/3966; A61B 2090/3983
See application file for complete search history.

(56) References Cited

U.S. PATENT DOCUMENTS

| | | | | |
|---|---|---|---|---|
| 7,729,772 | B2* | 6/2010 | Williams | A61N 1/0551 607/41 |
| 10,994,139 | B2* | 5/2021 | Fayram | A61N 1/36062 |
| 11,648,405 | B2* | 5/2023 | Crites-Bachert | A61N 1/372 606/129 |
| 2008/0039866 | A1* | 2/2008 | Stetz | A61B 90/39 600/407 |
| 2011/0191084 | A1* | 8/2011 | Cooke | A61B 6/466 703/11 |
| 2016/0324539 | A1* | 11/2016 | Sahhar | A61B 17/3403 |

(Continued)

*Primary Examiner* — Eric D. Bertram
(74) *Attorney, Agent, or Firm* — Fleit Intellectual Property Law; Jon Gibbons; Paul D. Bianco (57) ABSTRACT

Practitioners who use sacral neuromodulation on a regular basis have sought ways to simplify the procedure and performing percutaneous nerve evaluations in the office setting have become increasingly more popular. However, many practitioners are limited by the lack of availability of fluoroscopy or similar imaging systems in the office setting and do not feel comfortable executing the procedure without it, for a variety of reasons. The disclosed system and method demonstrate an avenue to circumvent the lack of fluoroscopic guidance in the office setting enabling execution of percutaneous nerve evaluations successfully and efficiently.

18 Claims, 5 Drawing Sheets

(56) References Cited

U.S. PATENT DOCUMENTS

| | | | | |
|---|---|---|---|---|
| 2017/0333153 | A1* | 11/2017 | Halpert | B43K 29/08 |
| 2018/0133473 | A1* | 5/2018 | Yoo | A61N 2/02 |
| 2020/0008762 | A1* | 1/2020 | Crites-Bachert | A61B 90/39 |
| 2020/0405399 | A1* | 12/2020 | Steinberg | G06N 20/00 |
| 2021/0077047 | A1* | 3/2021 | Tolkowsky | G06T 7/33 |
| 2021/0128926 | A1 | 5/2021 | Crites-Bachert | |
| 2021/0386480 | A1* | 12/2021 | Tolkowsky | A61B 46/20 |
| 2022/0110698 | A1* | 4/2022 | Tolkowsky | A61B 34/25 |

* cited by examiner

PERCUTANEOUS NERVE EVALUATION FOR SACRAL NEUROMODULATION

CROSS REFERENCE TO RELATED APPLICATIONS

This application claims priority to U.S. patent application Ser. No. 17/083,774, filed Oct. 29, 2020, now U.S. Pat. No. 11,648,405, the teaching of this patent application is hereby incorporated by reference in their entirety

FIELD OF THE DISCLOSURE

The disclosure relates to percutaneous nerve evaluations for sacral neuromodulation.

BACKGROUND

Electrical stimulation of somatic afferent pathways in the sacral spinal roots (as well as the pudendal nerve or posterior tibial nerve) can inhibit bladder activity in both humans and animals and therefore can be clinically effective in treating overactive bladder symptoms. Stimulation of the sacral S3 spinal root is currently an FDA approved therapy for the lower urinary tract disorders including bladder overactivity, urgency, frequency, incontinence, and urinary retention. Stimulation is also an FDA approved therapy for bowel control. Although the mechanisms underlying neuromodulation are not totally understood, this type of therapy has become popular because bowel control and lower urinary tract dysfunctions can be more effectively managed in some patients than treatment with medication alone.

In order to determine whether neuromodulation is appropriate for a particular patient, the patient typically undergoes an evaluation. As an increasing number of practitioners are offering this treatment modality, ways to simplify the process of the trial evaluation have been explored and proposed. Percutaneous nerve evaluations, also known as basic evaluations, have emerged as a means for patients to undergo a relatively non-invasive trial of neuromodulation. In fact, percutaneous nerve evaluations have increased in use as more practitioners have elected to implement the trials in the office setting, as opposed to a hospital facility or a surgical center.

The trial procedure can be readily executed in the office setting with a local anesthesia, thus sparing the patient the expense of a hospital or surgery center as well as more aggressive sedation. Traditionally, fluoroscopic guidance has been used. However, when fluoroscopy or similar imaging is not available, a practitioner must either forego the possibility of the procedure or develop an alternative approach. For this reason, a number of techniques to identify, palpate, and mark sacral landmarks as well as the use of ultrasound guidance have emerged to circumvent the need for fluoroscopy or similar imaging. While many practitioners have adopted these techniques, others have not elected to use such methods for a variety of reasons. Faced with the dilemma of not having fluoroscopy or similar imaging available in the office setting, a reliable system and method to execute percutaneous nerve evaluations in the office setting has been developed by the inventor and is disclosed herein.

SUMMARY OF THE DISCLOSURE

A method for positioning a foramen needle to implant a trial lead for percutaneous nerve evaluation for sacral neuromodulation of a patient is disclosed.

In an embodiment, the method comprises: visualizing with an imaging system located in an imaging room an anterior/posterior view of a sacral region of the patient, with the imaging system providing an image of the foramen; positioning a radio-opaque rod on the skin of the patient above the most medial edge of a first selected sacral foramen while visualizing the anterior/posterior view; using the radio-opaque rod as a straight edge to draw a first medial line on the skin of the patient while visualizing the anterior/posterior view; positioning the radio-opaque rod or a different radio-opaque rod on the skin of the patient above the midline of the first selected sacral foramen while visualizing the anterior/posterior view; using the radio-opaque rod as a straight edge to draw a first lateral line on the skin of the patient while visualizing the anterior/posterior view; visualizing with the imaging system located in the imaging room a lateral view of the sacral region of the patient; positioning a radio-opaque pointer on the skin of the patient pointing to a superior aspect of the first selected sacral foramen; using the radio-opaque pointer as a guide to draw a first superior line on the skin of the patient while visualizing the lateral view, the first superior line substantially perpendicular to and intersect the first medial line and the first lateral line; positioning the radio-opaque pointer or a different radio-opaque pointer on the skin of the patient pointing to an inferior aspect of the first selected sacral foramen; using the radio-opaque pointer as a guide to draw a first inferior line on the skin of the patient while visualizing the lateral view, the first inferior line substantially perpendicular to and intersect the first medial line and the first lateral line so that an area between the intersecting first medial, first lateral, first superior, and first inferior lines create a first target box; and using the first target box as a guide, inserting a first foramen needle through the skin of the patient until the first foramen needle drops into the first selected sacral foramen. The first foramen needle is inserted in a procedure room at a location different than the imaging room, and wherein the insertion of the first foramen needle is performed without the use of imaging equipment.

The first medial line can be drawn by tracing a marking implement against the radio-opaque rod. The first foramen needle can be inserted through the first target box.

For bilateral procedures, the method also includes: positioning the radio-opaque rod on the skin of the patient above the most medial edge of a second selected sacral foramen while visualizing the anterior/posterior view; using the radio-opaque rod as a straight edge to draw a second medial line on the skin of the patient while visualizing the anterior/posterior view; positioning the radio-opaque rod on the skin of the patient above the midline of the second selected sacral foramen while visualizing the anterior/posterior view; using the radio-opaque rod as a straight edge to draw a second lateral line on the skin of the patient while visualizing the anterior/posterior view; drawing a second superior line on the skin of the patient, the second superior line substantially perpendicular to and intersect the second medial line and the second lateral line; drawing a second inferior line on the skin of the patient, the second inferior line substantially perpendicular to and intersect the second medial line and the second lateral line so that an area between the intersecting second medial, second lateral, second superior, and second inferior lines create a second target box; and using the second target box as a guide, inserting a second foramen needle through the skin of the patient until the second foramen needle drops into the second selected sacral foramen. The second foramen needle is inserted in the procedure room free of fluoroscopic imaging equipment.

In an exemplary embodiment, the first and second medial lines and the first and second lateral lines are drawn before the first and second superior and the first and second inferior lines are drawn. The first and second medial lines can be drawn before the first and second lateral lines.

In one embodiment, the second superior line is drawn by continuing the first superior line and the second inferior line is drawn by continuing the first inferior line. In another embodiment, the second superior line is drawn by positioning the radio-opaque pointer on the skin of the patient pointing to a superior aspect of the second selected sacral foramen and using the radio-opaque pointer as a guide while visualizing the lateral view and the second inferior line is drawn by positioning the radio-opaque pointer on the skin of the patient pointing to an inferior aspect of the second selected sacral foramen and using the radio-opaque pointer as a guide while visualizing the lateral view.

For certain clinical applications, the first selected sacral foramen is one of the third sacral right foramen and the third sacral left foramen and the second selected sacral foramen is the other of the third sacral right foramen and the third sacral left foramen.

In some embodiments, the patient is not sedated during the method. The method can further comprise placing the trial lead through the first foramen needle into the first selected sacral foramen, with the trial lead including one or more electrodes. The patient can experience anal bellow and toe flexion on the one or more electrodes at 2 mA of less of stimulation.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein.

DETAILED DESCRIPTION

As required, embodiments are disclosed herein; however, it is to be understood that the disclosed embodiments are merely examples and that the methods described below can be embodied in various forms. Therefore, specific structural and functional details disclosed herein are not to be interpreted as limiting, but merely as a representative basis for teaching one skilled in the art to variously employ the present subject matter in virtually any appropriately detailed structure and function. Further, the terms and phrases used herein are not intended to be limiting, but rather, to provide an understandable description of the concepts.

It can be advantageous to set forth definitions of certain words and phrases used throughout this disclosure. The terms "a" or "an", as used herein, are employed to describe elements and components described herein. This is done merely for convenience and to give a general sense of the scope of the disclosure. This description should be read to include one or at least one and the singular also includes the plural unless it is obvious that it is meant otherwise. The term plurality, as used herein, is defined as two or more than two. The term another, as used herein, is defined as at least a second or more.

The term "communicate," as well as derivatives thereof, encompasses both direct and indirect communication. The terms "include" and "comprise," as well as derivatives thereof, mean inclusion without limitation. The term "or" is inclusive, meaning and/or. The phrase "associated with," as well as derivatives thereof, can mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items can be used, and only one item in the list can be needed. For example, "at least one of: A, B, and C" includes any of the following combinations: A, B, or C; A and B; A and C; B and C; and A, B, and C.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. As used herein, the terms "substantial" and "substantially" means, when comparing various parts to one another, that the parts being compared are equal to or are so close enough in dimension that one skill in the art would consider the same. Substantial and substantially, as used herein, are not limited to a single dimension and specifically include a range of values for those parts being compared. The range of values, both above and below (e.g., "+/−" or greater/lesser or larger/smaller), includes a variance that one skilled in the art would know to be a reasonable tolerance for the parts mentioned.

Note that not all of the activities described above in the general description or the examples are required, that a portion of a specific activity may not be required, and that one or more further activities can be performed in addition to those described. Still further, the order in which activities are listed are not necessarily the order in which they are performed.

The disclosure relates generally to a novel system and method for percutaneous nerve evaluations for sacral neuromodulation. The disclosed system and method allow a practitioner to utilize the benefits of sophisticated imaging for percutaneous nerve evaluations without needing dedicated imaging equipment in the procedure room in which the trial lead is actually implanted. This is achieved in a staged procedure. The first phase is conducted in an imaging suite, which can be located at a hospital or surgical center, which typically has one or more imaging systems. The second phase is conducted in a procedure room, which can be located at a doctor's office or any suitable location that does not have imaging equipment accessible during the second phase.

Figure 1:
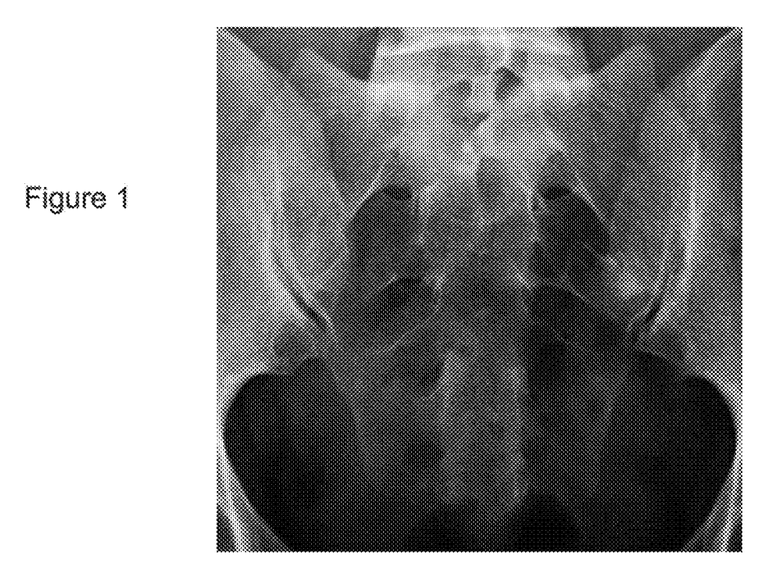
FIG. 1 is an anterior-posterior fluoroscopic image of the sacrum.
Figure 2:
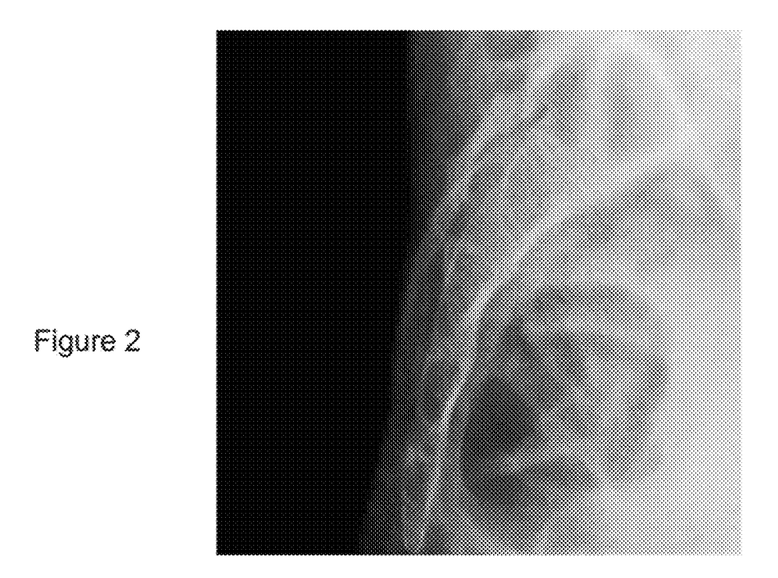
FIG. 2 is a lateral fluoroscopic image of the sacrum.

FIGS. 1 and 2 show fluoroscopic images of the sacral region. Although this embodiment uses fluoroscopy, the disclosure contemplates the use of other imaging modalities, such as digital x-rays or any other suitable imaging system that obtains the images needed for the method as disclosed herein. As noted above, the fluoroscopic images of FIGS. 1 and 2, as well as those in FIGS. 3, 4, 6, and 7 and the resulting skin marks in FIGS. 5 and 8, are taken in an imaging suite located at a hospital, surgical center, or any other location with the resources to support the expense and safety protocols required by the imaging equipment. One exemplary embodiment of a suitable fluoroscopic imaging apparatus is commonly known as a C-arm.

Figure 3:
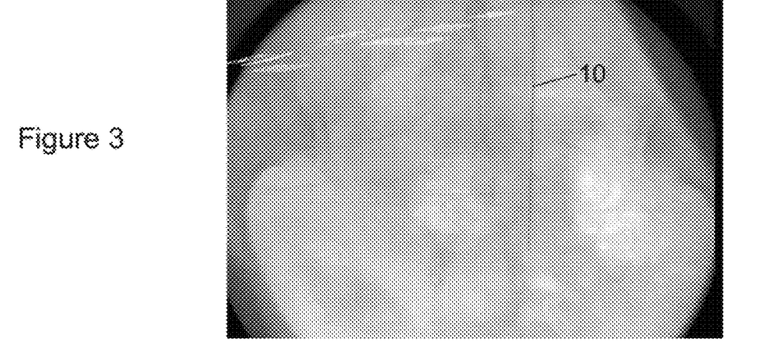
FIG. 3 is an anterior-posterior fluoroscopic image with a radio-opaque rod placed on the skin above the most medial edge of the third sacral right foramen.
Figure 4:
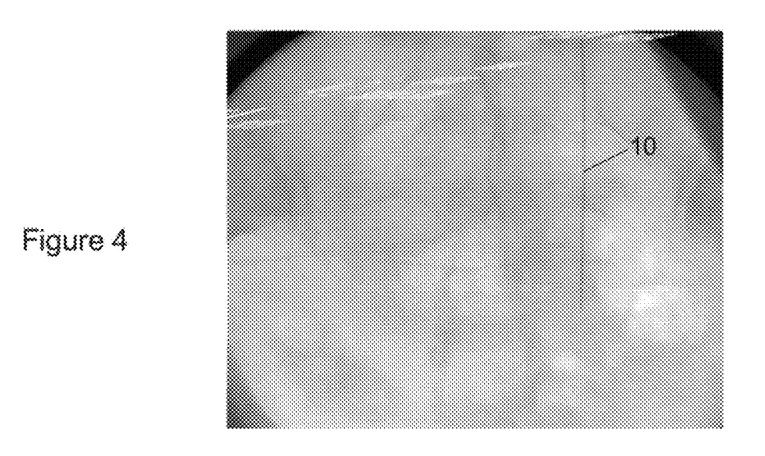
FIG. 4 is an anterior-posterior fluoroscopic image with a radio-opaque rod placed on the skin above the midline of the third sacral right foramen.
Figure 5:
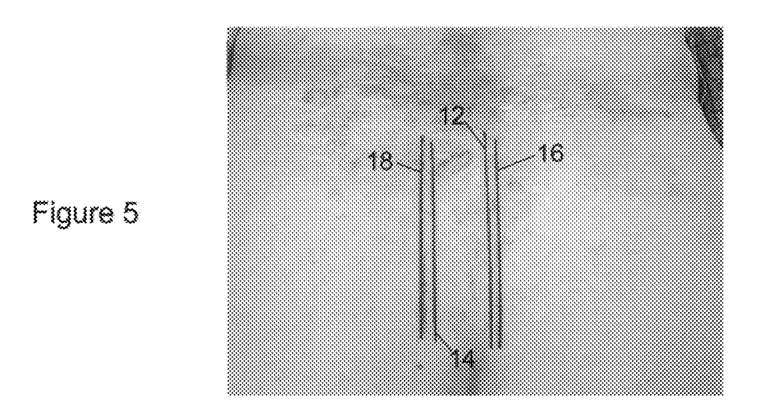
FIG. 5 is a photograph showing bilateral lines made on the skin with the anterior-posterior fluoroscopic images of FIGS. 3 and 4.

Referring to FIGS. 3-5, a patient arrives at the imaging suite and is prepared in a conventional manner, and as is also well-known, positioned on a table in the prone position with pillows and/or bolsters under the abdomen of the patient to flatten the sacral area as shown in FIG. 1. Using fluoroscopy imaging, a radio-opaque rod 10 is placed on the skin above the most medial edge of the third sacral right foramen to represent the most medial aspect for which the needle ideally could be placed to implant the trial lead for percutaneous nerve evaluation. Although radio-opaque rod 10 is shown in the figures, any radio-opaque implement that is suitable to serve as a guide for the practitioner can be used.

The third sacral foramen is a relevant anatomical location for percutaneous nerve evaluation for sacral neuromodulation as it generally provides access to the third sacral spinal nerve, which is targeted for bladder and bowel control. In some individuals, other sacral foramen (e.g. sacral #2 foramen or sacral #4 foramen) provide better access to the third sacral spinal nerve. In other cases, a different nerve may be selected for neuromodulation. Accordingly, the present disclosure contemplates access through other foramen and neuromodulations of other nerves. In particular, the disclosure contemplates other sacral locations, such as the fourth sacral foramen, as well as other spinal locations (e.g. lumbar, thoracic and cervical) associated with percutaneous nerve evaluation for other diagnostic and/or therapeutic procedures.

Using radio-opaque rod 10 as a straight edge, the practitioner draws a line 12 on the skin of the patient. Any suitable marker or similar implement can be used to make line 12 or any of the other lines and/or marks discussed below. If only one foramen is of interest, the disclosure contemplates that either the left or right foramen can be used. The disclosure also contemplates a bilateral procedure so that both the left and right foramina are used. If a bilateral procedure is to be performed, the practitioner can start initially with either the right or left foramen.

It should be noted that line 12 as well as any of the other skin markings as disclosed herein do not necessarily correlate to the exact distance appearing on fluoroscopy as there is space between the skin and the sacrum secondary to tissue. The concept is to measure on the skin for an approximation of where to insert the needle for appropriate placement of the trial lead for effective percutaneous nerve evaluation.

For the left foramen, the above-described process is repeated. In particular, fluoroscopy imaging is used to place radio-opaque rod 10 on the skin above the most medial edge of the third sacral left foramen to represent the most medial aspect for which the needle ideally could be placed to implant the trial lead for percutaneous nerve evaluation. Using radio-opaque rod 10 as a straight edge, the practitioner draws a line 14 on the skin of the patient.

As shown in FIG. 4, radio-opaque rod 10 is placed on the skin above the midline of the third sacral right foramen under anterior-posterior fluoroscopy imaging to identify the most lateral aspect of the desired needle placement to implant the trial lead for percutaneous nerve evaluation. Using radio-opaque rod 10 as a straight edge, the practitioner draws a line 16 on the skin of the patient. This process is repeated for the third sacral left foramen by placing radio-opaque rod 10 on the skin above the midline of the third sacral left foramen under anterior-posterior fluoroscopy imaging to identify the most lateral aspect of the desired needle placement to implant the trial lead for percutaneous nerve evaluation and drawing a line 18 on the skin of the patient using radio-opaque rod 10 as a guide.

As lines 12, 14, 16, and 18 can be drawn in any order, the order of the above-disclosed processes can be varied. Further the length of vertical lines 12, 14, 16, and 18 can also be varied as long as lines 12, 14, 16, and 18 intersect the horizontal lines, which will now be described.

Figure 6:
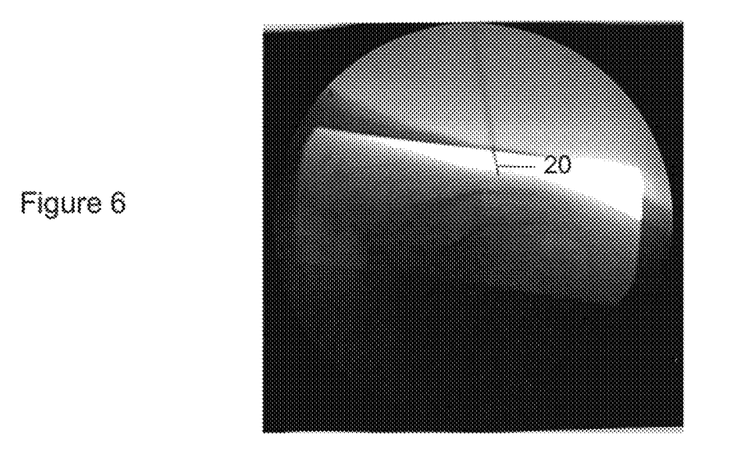
FIG. 6 is lateral fluoroscopic image with a radio-opaque pointer placed on the skin pointing to the superior aspect of the third sacral right foramen.
Figure 7:
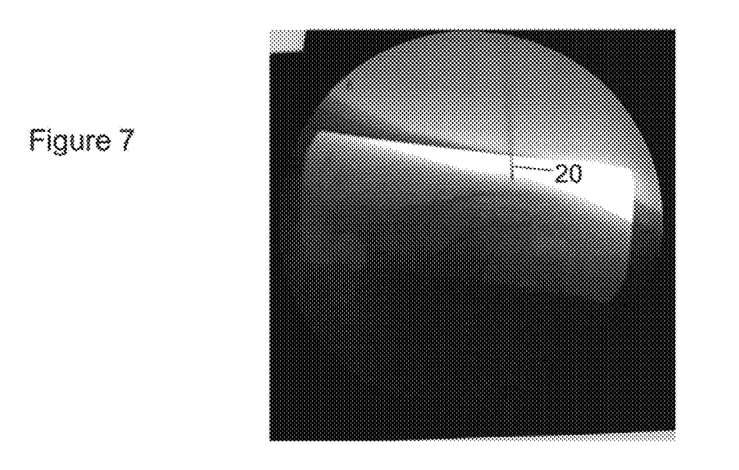
FIG. 7 is lateral fluoroscopic image with a radio-opaque pointer placed on the skin pointing to the inferior aspect of the third sacral right foramen.
Figure 8:
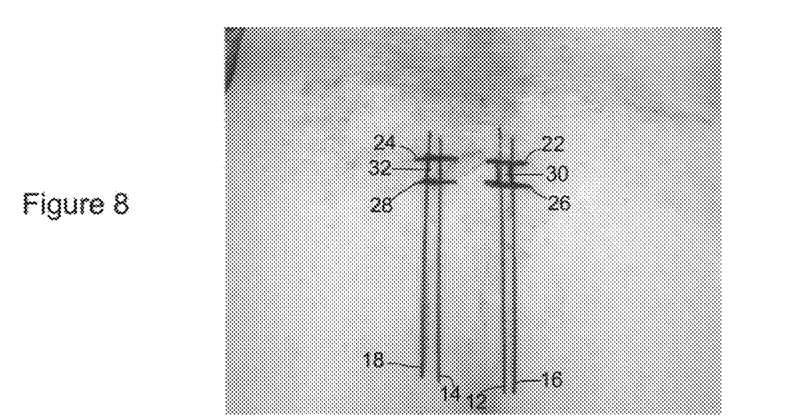
FIG. 8 is a photograph showing bilateral "target" boxes made on the skin with the fluoroscopic images of FIGS. 3 and 4 and FIGS. 7 and 8.

Referring to FIGS. 6-8, horizontal lines 22, 24, 26, and 28 are made under lateral fluoroscopic imaging. This can be done by moving the fluoroscopic imaging apparatus to completely visualize the sacrum in a lateral view. Alternatively, the patient can be placed in a lateral position by moving the patient onto the patient's side with the legs flexed to an approximately 90-degree angle to create a straight profile of the lateral sacrum on the table as shown in FIG. 2.

Using fluoroscopy imaging, a radio-opaque pointer 20 is placed on the skin pointing to the superior aspect of the third sacral right foramen to represent the most superior aspect for which the needle ideally could be placed to implant the trial lead for percutaneous nerve evaluation. Although radio-opaque pointer 20 is shown in the figures, any radio-opaque implement (including radio-opaque rod 10) that is suitable to serve as a guide for the practitioner can be used.

Using radio-opaque pointer 20 as a guide, the practitioner draws a line 22 on the skin of the patient to be approximately perpendicular to and intersect both line 12 and line 16. If desired, line 22 can be extended to also intersect line 14 and line 18. Even if the practitioner does not extend line 22 to also intersect line 14 and line 18, the practitioner can use the location of line 22 to freehand drawing line 24 to limit the number of images. Alternatively, the patient can be positioned on their other side with the legs flexed to an approximately 90-degree angle or the fluoroscopic imaging apparatus is moved to the other side of the patient to completely visualize the sacrum in a lateral view. Radio-opaque pointer 20 is placed on the skin pointing to the superior aspect of the third sacral left foramen to represent the most superior aspect for which the needle ideally could be placed to implant the trial lead for percutaneous nerve evaluation. Using radio-opaque pointer 20 again as a guide, the practitioner draws a line 24 on the skin of the patient to be approximately perpendicular to and intersect both line 12 and line 16 to denote the most superior aspect of the third sacral left foramen.

Using fluoroscopy imaging, radio-opaque pointer 20 is placed on the skin pointing to the inferior aspect or bone seam of the third sacral right foramen to represent the most inferior aspect for which the needle ideally could be placed to implant the trial lead for percutaneous nerve evaluation. Using radio-opaque pointer 20 as a guide, the practitioner draws a line 26 on the skin of the patient to be approximately perpendicular to and intersect both line 12 and line 16. The intersection of lines 22 and line 26 with line 12 and line 16 creates a first target box 30 on the skin. First target box 30 denotes an area on the patient's skin to enable needle placement at an approximate 45-degree angle to implant the trial lead for percutaneous nerve evaluation.

If desired, line 26 can be extended to also intersect line 14 and line 18. Even if the practitioner does not extend line 26 to also intersect line 14 and line 18, the practitioner can use the location of line 26 to freehand drawing line 28 to limit the number of images. Alternatively, the patient can be positioned on their other side with the legs flexed to an approximately 90-degree angle or the fluoroscopic imaging apparatus is moved to the other side of the patient to completely visualize the sacrum in a lateral view. Radio-opaque pointer 20 is placed on the skin pointing to the inferior aspect or bone seam of the third sacral left foramen to represent the most inferior aspect for which the needle ideally could be placed to implant the trial lead for percutaneous nerve evaluation. Using radio-opaque pointer 20 again as a guide, the practitioner draws a line 28 on the skin of the patient to be approximately perpendicular to and intersect both line 14 and line 18. The intersection of line 24 and line 28 with line 14 and line 18 creates a second target box 32 on the skin. Second target box 32 denotes an area on the patient's skin to enable needle placement at an approximate 45-degree angle to implant the trial lead for percutaneous nerve evaluation.

As lines 22, 24, 26, and 28 can be drawn in any order, the order of the above-disclosed processes can be varied. Further the length of horizontal lines 22, 24, 26, and 28 can also be varied as long as line 22 and line 26 both intersect lines line 12 and line 16 to create first target box 30 and line 24 and line 28 both intersect lines line 14 and line 18 to create second target box 32. Once either first target box 30 or second target box 32 is created for a unilateral percutaneous nerve evaluation or both first target box 30 and second target box 32 are created for a bilateral percutaneous nerve evaluation, imaging is no longer needed for the disclosed method and system.

Accordingly, the patient is taken to a procedure room in which the trial lead is actually implanted. The procedure room can be located at a doctor's office or any suitable location that does not have the imaging equipment used to make the skin markings accessible during the trial lead implantation.

Figure 9:
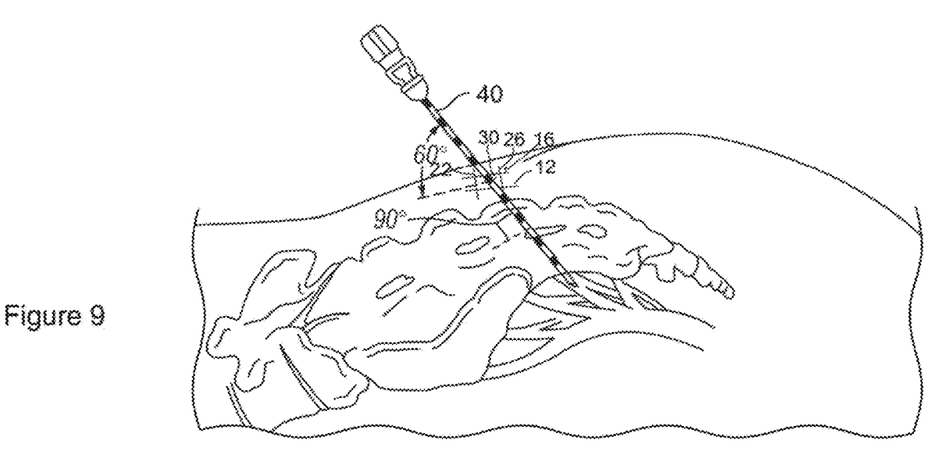
FIG. 9 is a drawing showing a foramen needle in one of the target boxes.
Figure 10:
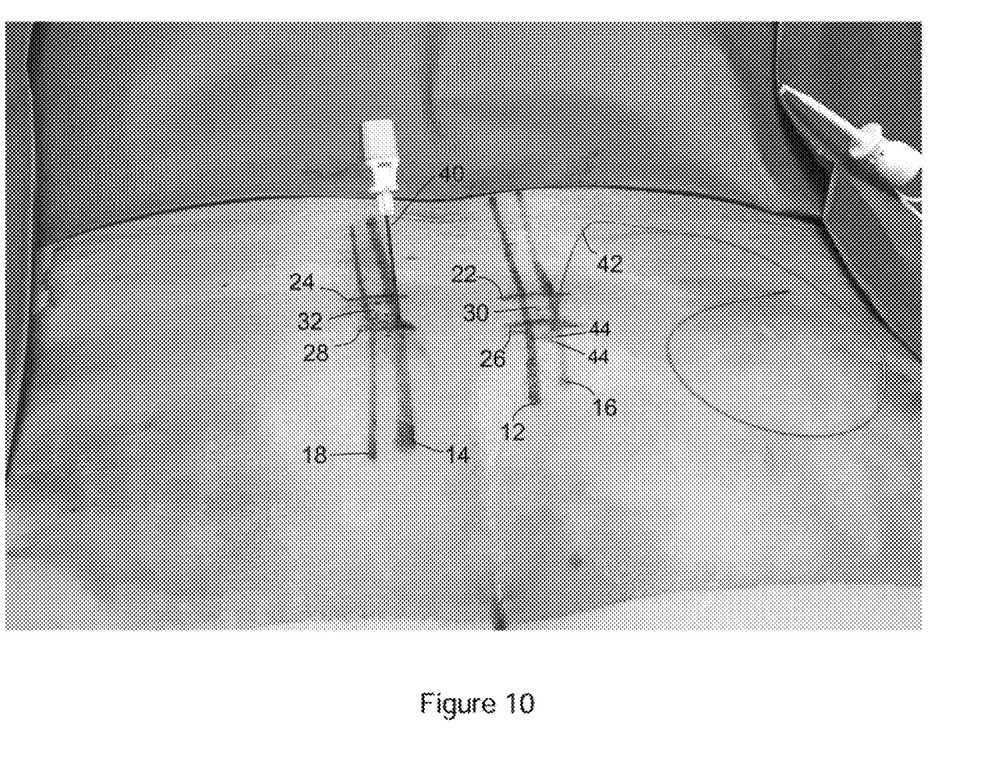
FIG. 10 is a photograph showing the foramen needle in one of the target boxes and the implanted trial lead in the opposite side of the spine.

After the patient is prepped and draped in the standard fashion, a local anesthetic agent (such as for example a 2% lidocaine solution) is applied to the area around either first target box 30 or second target box 32 for a unilateral percutaneous nerve evaluation or both first target box 30 and second target box 32 for a bilateral percutaneous nerve evaluation. With reference to FIGS. 9 and 10, the practitioner then begins placing a foramen needle 40 through the skin at an approximately 45-degree angle (approximate range of about 35-degrees to about 70-degrees) using either target box 30 or target box 32 as a guide. Foramen needle 40 is advanced until needle 40 drops into the sacral #3 foramen below the anterior surface. The needle angle insertion may be varied depending on the patient's body habitus.

As is known, the practitioner can test needle 40 for optimal placement resulting in the patient experiencing anal bellows and toe flexion at 2 mA or less of stimulation. The practitioner can continue to adjust needle 40 using minute movements and angle changes until the desired motion and sensory response is achieved.

Once this is achieved, the practitioner places a trail lead 42 with one or more electrodes 44 (shown schematically since they are under the skin and would not be visible in the photograph) into the sacral #3 foramen through needle 40 according to standard procedure. The practitioner can conduct another test with trial lead 42 to ensure the patient experiences anal bellows and toe flexion on all electrodes 44 at 2 mA or less of stimulation. If this is not achieved, the practitioner can remove trial lead 42 and begin with needle placement again until the desired response is achieved with trial lead 42.

Experimental results on 55-65 patients (suffering from either frequency/urgency, urge incontinence, or fecal incontinence) have shown the promise of the disclosed system and method. Specifically, it was found that each of the patient skin markings was accurate to within 5-6 mm from the "target box" of the actual needle placement for the patient to experience toe flexion, anal bellows, and feel sensation in the "bicycle seat" area at ≤3 m Amp. Additionally, it was noted that the percutaneous nerve evaluations performed had a mean time of under 12 minutes (8.2-20.8 minutes) to complete, including securing the wires to the patient's skin. None of the patients received any kind of pre-procedural sedation, and all patients but three (two of which suffer from chronic pain) tolerated the procedure an average of 5.16/10 on a 10-point Likert scale. With the exception of the chronic pain patient, all patients reported that they would undergo the office procedure again, and none of the patients required pain medication stronger than Tylenol/Ibuprofen post procedure. All patients except one patient (over 97%) converted to full implant after each voiding diary revealed ≥50% improvement in symptoms.

All references cited herein are expressly incorporated by reference in their entirety. It will be appreciated by persons skilled in the art that the present disclosure is not limited to what has been particularly shown and described herein above. In addition, unless mention was made above to the contrary, it should be noted that all of the accompanying drawings are not to scale. There are many different features to the present disclosure and it is contemplated that these features may be used together or separately. Thus, the disclosure should not be limited to any particular combination of features or to a particular application of the disclosure. Further, it should be understood that variations and modifications within the spirit and scope of the disclosure might occur to those skilled in the art to which the disclosure pertains.

In this regard, the procedure can be modified such that instead of making a complete "target box," a practitioner could simply use a radio-opaque pointer to simply make a mark in the AP and lateral views on the patient's skin and then place the needle "in the vicinity" of the marking.

Accordingly, all expedient modifications readily attainable by one versed in the art from the disclosure set forth herein that are within the scope and spirit of the present disclosure are to be included as further embodiments of the present disclosure.

The description in the present application should not be read as implying that any particular element, step, or function is an essential or critical element that must be included in the claim scope. The scope of patented subject matter is defined only by the allowed claims. Moreover, none of the claims invokes 35 U.S.C. § 112(f) with respect to any of the appended representative claims or claim elements unless the exact words "means for" or "step for" are explicitly used in the particular claim, followed by a participle phrase identifying a function.

Benefits, other advantages, and solutions to problems have been described above with regard to specific embodiments. However, the benefits, advantages, solutions to problems, and any feature(s) that can cause any benefit, advantage, or solution to occur or become more pronounced are not to be construed as a critical, required, sacrosanct or an essential feature of any or all the claims.

After reading the disclosure, skilled artisans will appreciate that certain features are, for clarity, described herein in the context of separate embodiments, can also be provided in combination in a single embodiment. Conversely, various features that are, for brevity, described in the context of a single embodiment, can also be provided separately or in any sub-combination. Further, references to values stated in ranges include each and every value within that range.

The above discussion is meant to be illustrative of the principles and various embodiments of the present invention. Numerous variations and modifications will become apparent to those skilled in the art once the above disclosure is fully appreciated. It is intended that the following be interpreted to embrace all such variations and modifications.

What is claimed is:

1. A method for positioning a foramen needle to implant a trial lead for percutaneous nerve evaluation for sacral neuromodulation of a patient, the method comprising:
   visualizing with an imaging system an anterior/posterior view of a sacral region of the patient, the imaging system located in an imaging room and providing an image of the foramen;
   positioning a radio-opaque rod on the skin of the patient above the most medial edge of a first selected sacral foramen while visualizing the anterior/posterior view;
   using the radio-opaque rod as a straight edge to draw a first medial line on the skin of the patient while visualizing the anterior/posterior view;
   positioning the radio-opaque rod or a different radio-opaque rod on the skin of the patient above the midline of the first selected sacral foramen while visualizing the anterior/posterior view;
   using the radio-opaque rod as a straight edge to draw a first lateral line on the skin of the patient while visualizing the anterior/posterior view;
   visualizing with the imaging system located in the imaging room a lateral view of the sacral region of the patient;
   positioning a radio-opaque pointer on the skin of the patient pointing to a superior aspect of the first selected sacral foramen;
   using the radio-opaque pointer as a guide to draw a first superior line on the skin of the patient while visualizing the lateral view, the first superior line substantially perpendicular to and intersect the first medial line and the first lateral line;
   positioning the radio-opaque pointer or a different radio-opaque pointer on the skin of the patient pointing to an inferior aspect of the first selected sacral foramen;
   using the radio-opaque pointer as a guide to draw a first inferior line on the skin of the patient while visualizing the lateral view, the first inferior line substantially perpendicular to and intersect the first medial line and the first lateral line so that an area between the intersecting first medial, first lateral, first superior, and first inferior lines create a first target box;
   using the first target box as a guide, inserting a first foramen needle through the skin of the patient until the first foramen needle drops into the first selected sacral foramen,
   wherein the first foramen needle is inserted in a procedure room at a location different than the imaging room, and wherein the insertion of the first foramen needle is performed without use of imaging equipment.

2. The method of claim 1, wherein the first medial line is drawn by tracing a marking implement against the radio-opaque rod.

3. The method of claim 1, wherein the first foramen needle is inserted through the first target box.

4. The method of claim 1, further comprising:
   positioning the radio-opaque rod on the skin of the patient above the most medial edge of a second selected sacral foramen while visualizing the anterior/posterior view;
   using the radio-opaque rod as a straight edge to draw a second medial line on the skin of the patient while visualizing the anterior/posterior view;
   positioning the radio-opaque rod on the skin of the patient above the midline of the second selected sacral foramen while visualizing the anterior/posterior view;
   using the radio-opaque rod as a straight edge to draw a second lateral line on the skin of the patient while visualizing the anterior/posterior view;
   drawing a second superior line on the skin of the patient, the second superior line substantially perpendicular to and intersect the second medial line and the second lateral line;
   drawing a second inferior line on the skin of the patient, the second inferior line substantially perpendicular to and intersect the second medial line and the second lateral line so that an area between the intersecting second medial, second lateral, second superior, and second inferior lines create a second target box;
   using the second target box as a guide, inserting a second foramen needle through the skin of the patient until the second foramen needle drops into the second selected sacral foramen, wherein the second foramen needle is inserted in the procedure room free of fluoroscopic imaging equipment.

5. The method of claim 4, wherein the first and second medial lines and the first and second lateral lines are drawn before the first and second superior and the first and second inferior lines are drawn.

6. The method of claim 5, wherein the first and second medial lines are drawn before the first and second lateral lines.

7. The method of claim 5, wherein the second superior line is drawn by continuing the first superior line and the second inferior line is drawn by continuing the first inferior line.

8. The method of claim 4, wherein the second superior line is drawn by positioning the radio-opaque pointer on the skin of the patient pointing to a superior aspect of the second selected sacral foramen and using the radio-opaque pointer as a guide while visualizing the lateral view and wherein the second inferior line is drawn by positioning the radio-opaque pointer on the skin of the patient pointing to an inferior aspect of the second selected sacral foramen and using the radio-opaque pointer as a guide while visualizing the lateral view.

9. The method of claim 4, wherein the first selected sacral foramen is one of the third sacral right foramen and the third sacral left foramen and the second selected sacral foramen is the other of the third sacral right foramen and the third sacral left foramen.

10. The method of claim 1, wherein the patient is not sedated.

11. The method of claim 1, further comprising placing the trial lead through the first foramen needle into the first selected sacral foramen.

12. The method of claim 11, wherein the trial lead includes one or more electrodes.

13. The method of claim 12, wherein the patient experiences anal bellow and toe flexion on the one or more electrodes at 2 mA of less of stimulation.

14. A method for positioning a foramen needle to implant a trial lead for percutaneous nerve evaluation for neuromodulation of a patient, the method comprising:
    visualizing with an imaging system located in an imaging room an anterior/posterior view of a spinal region of the patient, the imaging system providing an image of the foramen;
    positioning a radio-opaque rod on the skin of the patient above the most medial edge of a first selected foramen while visualizing the anterior/posterior view;
    using the radio-opaque rod as a straight edge to draw a first medial line on the skin of the patient while visualizing the anterior/posterior view;
    positioning the radio-opaque rod or a different radio-opaque rod on the skin of the patient above the midline of the first selected foramen while visualizing the anterior/posterior view;
    using the radio-opaque rod as a straight edge to draw a first lateral line on the skin of the patient while visualizing the anterior/posterior view;
    visualizing with fluoroscopy located in the imaging room a lateral view of the spinal region of the patient;
    positioning a radio-opaque pointer on the skin of the patient pointing to a superior aspect of the first selected foramen;
    using the radio-opaque pointer as a guide to draw a first superior line on the skin of the patient while visualizing the lateral view, the first superior line substantially perpendicular to and intersect the first medial line and the first lateral line;
    positioning the radio-opaque pointer or a different radio-opaque pointer on the skin of the patient pointing to an inferior aspect of the first selected foramen;
    using the radio-opaque pointer as a guide to draw a first inferior line on the skin of the patient while visualizing the lateral view, the first inferior line substantially perpendicular to and intersect the first medial line and the first lateral line so that an area between the intersecting first medial, first lateral, first superior, and first inferior lines create a first target box;
    using the first target box as a guide, inserting a first foramen needle through the skin of the patient until the first foramen needle drops into the first selected foramen,
    wherein the first foramen needle is inserted in a procedure room at a location different than the imaging room, and wherein the insertion of the first foramen needle is performed without use of imaging equipment.

15. The method of claim 14, wherein the patient is not sedated.

16. The method of claim 14, further comprising placing the trial lead through the first foramen needle into the first selected sacral foramen.

17. The method of claim 16, wherein the trial lead includes one or more electrodes.

18. The method of claim 17, wherein the patient experiences anal bellow and toe flexion on the one or more electrodes at 2 mA of less of stimulation.

* * * * *